United States Patent [19]

Onopchenko et al.

[11] 4,361,704

[45] Nov. 30, 1982

[54] PROCESS FOR PREPARING M,M'-DINITROBENZOPHENONE

[75] Inventors: Anatoli Onopchenko, Monroeville; Edward T. Sabourin, Allison Park; Charles M. Selwitz, Monroeville, all of Pa.

[73] Assignee: Gulf Research & Development Company, Pittsburgh, Pa.

[21] Appl. No.: 242,691

[22] Filed: Mar. 11, 1981

[51] Int. Cl.³ ............................................. C07C 45/61
[52] U.S. Cl. ..................................... 568/306; 568/305
[58] Field of Search ........................................ 568/306

[56] References Cited

U.S. PATENT DOCUMENTS 2,561,190  7/1951  Firestine .................. 568/306 X
3,542,862  11/1970  Chemerda et al. ........... 568/306 X
3,721,713  3/1973  Bloom ....................... 568/306

*Primary Examiner*—Natalie Trousof
*Assistant Examiner*—Vera C. Clarke
*Attorney, Agent, or Firm*—Deane E. Keith; Forrest D. Stine; Joseph J. Carducci

[57] ABSTRACT

A process for preparing m,m'-dinitrobenzophenone which comprises reacting benzophenone with nitric acid in oleum.

9 Claims, No Drawings

PROCESS FOR PREPARING M,M'-DINITROBENZOPHENONE

BACKGROUND OF THE INVENTION

1. Field of the Invention

The present invention relates to a process for preparing m,m'-dinitrobenzophenone which comprises reacting benzophenone with nitric acid in oleum.

2. Description of the Prior Art

When benzophenone is reacted with nitric acid, a product can be obtained containing an isomeric mixture of dinitrobenzophenones, including o,o'-, o,m'-, m,m'-, m,p'- and p,p'-dinitrobenzophenones, which, in turn, can be subjected to hydrogenation to obtain an isomeric mixture of the corresponding diaminobenzophenones. The latter mixture can be reacted with 3,4,3',4'-benzophenone tetracarboxylic dianhydride (BTDA) to obtain a polyimide resin. Although the m,m'-, m,p'- and p,p'-diamino benzophenones in said latter mixture will react satisfactorily with BTDA to form desired long-chain polyimide resins, the ortho-diaminobenzophenones will react with BTDA to a far lesser extent, resulting in a mixture of long and relatively short polyimide resins. This is believed to be the result of hydrogen bonding between an ortho amine hydrogen and the carbonyl, which reduces the basicity of the compound and renders the compound less reactive with BTDA. It would be highly desirable, therefore, to reduce the content of ortho-substituted isomers of dinitrobenzophenones and substantially increase the content of m,m'-dinitrobenzophenone in a mixture containing the same.

SUMMARY OF THE INVENTION

We have discovered that benzophenone can be reacted with nitric acid to obtain a product containing an isomeric mixture of dinitrobenzophenones predominating in m,m'-dinitrobenzophenone, while substantially reducing the content of the isomers containing an ortho-nitro substituent with virtual disappearance of the o,o'-dinitrobenzophenone, by a process wherein benzophenone is reacted with nitric acid in oleum while maintaining critical weight ratios of benzophenone, sulfuric acid and sulfur trioxide in the feed.

The critical weight ratio of benzophenone, sulfuric acid (as 100 percent sulfuric acid) and sulfur trioxide must be in the range of about 1:3:1 to about 1:25:5, but preferably in the range of about 1:2:2 to about 1:15:4. The sulfuric acid and sulfur trioxide employed can be satisfied by the use of oleum. By "oleum" we mean to include concentrated sulfuric acid containing sulfur trioxide. The amount of sulfur trioxide, on a weight basis relative to the total weight of sulfuric acid and sulfur trioxide, will be in the range to satisfy the critical weight ratios defined above, for example, in the range of about five to about 65 percent, preferably about 10 to about 35 percent. Oleum suitable for use herein can be prepared, for example, by adding gaseous or liquid $SO_3$ to concentrated sulfuric acid. It is believed that sulfur trioxide when dissolved in, or added to, sulfuric acid readily forms $H_2S_2O_7$ and higher polysulfuric acids [R. Gillespie, *J. Chem. Soc.*, 2493 (1950)].

In carrying out the process defined and claimed herein, benzophenone, nitric acid, sulfuric acid and sulfur trioxide are brought together, with the weight ratios of benzophenone, sulfuric acid and sulfur trioxide being within the critical ranges defined above. The amount of nitric acid is not critical and should be sufficient, stoichiometrically, to place one nitro group on each of the rings of the benzophenone being treated. To assure substantially complete reaction, amounts in excess of those required stoichiometrically to obtain dinitrobenzophenones can be used, for example, up to about 10 weight percent, or even higher. The concentration of the nitric acid used can vary over a wide range, for example from about 50 to about 100 weight percent aqueous nitric acid, preferably from about 67 to about 95 weight percent aqueous nitric acid.

The reaction can be carried out for example by stirring the reaction mixture while heating the same in a temperature range of about 5° to about 120° C., preferably about 10° to about 90° C., for about 10 minutes to about 120 hours, or even longer, preferably for about one-half to about 24 hours. In a preferred embodiment in order to further control the reaction to assure obtaining the desired isomeric distribution, the process is carried out in a plurality of stages. In a first stage, for example, the temperature is maintained in a range of about 5° to about 50° C., preferably about 10° to about 30° C., for about 10 minutes to about 10 hours, preferably for about one-half to about eight hours. In a second stage the reaction mixture is maintained in the temperature range of about 20° to about 120° C., preferably about 50° to about 90° C., for about one-half to about five hours, preferably about one to about three hours. The pressure is not critical and elevated pressures up to about 100 pounds per square inch gauge (about 0.7 MPa), or even higher, can be used, although atmospheric, or ambient, pressure is preferred.

The dinitrobenzophenones can be recovered from the reaction mixture in any suitable or convenient manner. For example, the reaction mixture can be poured over ice and the resulting slurry can be subjected to filtration. The resulting filter cake, comprising the isomeric mixture of dinitrobenzophenones, can be washed with an alkaline solution, such as sodium hydroxide, potassium hydroxide or ammonium hydroxide, and water, to remove possible contaminating materials therefrom, such as residual nitric acid, sulfuric acid, sulfur trioxide, organic acids, phenolics, etc., and dried. The filter cake will contain substantially high amounts of meta-dinitrobenzophenones, particularly m,m'-dinitrobenzophenones. The weight ratio of m,m'- to m,p'-dinitrobenzophenones will be in the range of about 90:10 to about 96:4, generally about 92:8 to about 94:6. The filter cake will contain no appreciable amounts of o,o'- or p,p'-dinitrobenzophenones. The weight percent of o,m'-dinitrobenzophenone will be substantially reduced and will amount, for example, to about 0 to about 15 weight percent, generally in the range of 0 to about five weight percent, of the filter cake, but, most preferably, about 0 to about two.

We believe that because we employ benzophenone, sulfuric acid and sulfur trioxide within the critical weight ratio ranges defined above a substantial amount of dinitrobenzophenones containing the ortho-nitro substituent that are formed during the process are converted to benzoic acids, phenolics, carbon dioxide and other caustic-soluble products, thereby affecting the isomeric distribution of the reaction product in favor of the dinitrobenzophenones which do not contain an ortho-nitro-substituent, particularly m,m'-dinitrobenzophenone. We have also found that when the weight ratio of benzophenone, sulfuric acid and $SO_3$ are used within the critical weight ratios defined herein, the reaction product at the end of the reaction period always contains sulfur trioxide, for example, in amounts in excess of about four weight percent, and as high as about 20 weight percent, or even higher, but generally about 10 to about 15 weight percent, based on the weight of the reaction product.

DESCRIPTION OF PREFERRED EMBODIMENTS

The process defined and claimed herein can be illustrated by the following.

EXAMPLE I

Two hundred grams of benzophenone were incrementally added over a period of one hour, while stirring, to 1200 grams of 90 weight percent of aqueous nitric acid while maintaining the temperature during addition between about 65° and 75° C. After addition of benzophenone was completed, the temperature of the mixture was raised to 90° C. and the reaction was permitted to continue at such temperature for three hours. The solution was cooled to room temperature (25° C.) and then poured, while stirring, over 200 grams of cracked-ice-water mixture. The precipitated solids were recovered by filtration, washed four times with water (1000 milliliters each time) until the final washings were essentially neutral, and then dried in a vacuum oven for 24 hours at 100° C. The cream-colored product recovered amounted to 299 grams, corresponding essentially to a yield of 100 percent. Analysis of the product by high performance liquid chromatography (HPLC) showed the following isomer distribution: 7.9 weight percent o,o'-dinitrobenzophenone, 29.7 weight percent o,m'-dinitrobenzophenone, 44.4 weight percent m,m'-dinitrobenzophenone, 17.2 weight percent m,p'-dinitrobenzophenone and 0.8 weight percent p,p'-dinitrobenzophenone.

EXAMPLE II

Herein 110 grams of benzophenone was added gradually, over a 30-minute period, while stirring, to 1100 grams of 98 weight percent aqueous sulfuric acid while maintaining the temperature, during the addition, at about 25° C. In another container, a nitrating mixture was prepared by gradually adding, over a 90-minute period, while stirring, 84 grams of 90 weight percent aqueous nitric acid to 276 grams of concentrated sulfuric acid, while maintaining the temperature of the mixture during the addition between about 20° and 25° C. The latter mixture was then added, by way of an addition funnel, to the dissolved benzophenone at a rate sufficient to maintain the temperature of the resulting mixture slightly below about 30° C. Upon completion of the addition, the resulting mixture was allowed to react at 30° C. for 30 minutes and then at 50° C. for 30 minutes and finally at 70° C. for 30 minutes. The product was cooled and worked up as in Example I, resulting in the production of 163.7 grams of dinitrobenzophenones, essentially 100 percent yield. Analysis of the product by HPLC showed the following: 2.5 weight percent o,o'-dinitrobenzophenone, 20.6 weight percent o,m'-dinitrobenzophenone, 65.2 weight percent m,m'-dinitrobenzophenone, 11.7 weight percent m,p'-dinitrobenzophenone and <0.1 weight percent p,p'-dinitrobenzophenone.

EXAMPLE III

A nitrating mixture was prepared by adding 165 grams of 90 weight percent aqueous nitric acid over a period of 30 minutes to 570 grams of well stirred oleum containing concentrated sulfuric acid and 22.5 weight percent sulfur trioxide while maintaining the temperature of the resulting mixture during the stirring procedure at about 10° to about 15° C. Two hundred grams of benzophenone were gradually dissolved over a period of 60 minutes in 1900 grams of oleum containing 22.5 weight percent sulfuric acid while maintaining the temperature of the resulting mixture at about 10° to about 20° C. With vigorous stirring and cooling the nitrating mixture of acids prepared above was gradually added to the benzophenone mixture over a period of 1.5 hours at about 10° to about 15° C. The resulting mixture was allowed to warm to 25° C. and was held at this temperature, with stirring, for a period of 30 minutes. An aliquot sample was taken up and analyzed for its isomeric dinitrobenzophenone content. The results are tabulated in Table I below under Example III (a). The remainder of the reaction mixture was heated to 70° C., at which point another sample was taken and analyzed. The results are tabulated in Table I as Example III(b). Reaction was continued with the remainder of the reaction mixture at 70° C. for an additional hour. Samples were taken at the end of each one-half hour and analyzed. These results are also tabulated in Table I as Examples III(c) and III(d), respectively. The resulting reaction product was cooled, poured over 2000 grams of cracked ice-water mixture and filtered. The recovered solids were washed twice, each time with 1000-milliliter portions of water, then with 1000 milliliters of 10 weight percent aqueous sodium hydroxide and finally twice, each time with 1000 milliliters of water, until the washings were found to be neutral. The solids were then dried in a vacuum oven at 100° C. for 16 hours, resulting in the recovery of 252 grams of dinitrobenzophenones, corresponding to a yield of 84 percent.

EXAMPLES IV to X

An additional series of runs was carried out following the procedure of Example III but wherein the weight ratios of benzophenone, sulfuric acid and sulfur trioxide in the feed were varied. Only the product at the end of the reaction, however, was analyzed.

The pertinent data from each of Examples I to X are summarized below in Table I.

TABLE I

| Run No. | Composition of Feed, Grams | | | | | Weight Ratio: BZP:H$_2$SO$_4$:SO$_3$ | Yield of DNBZP | Composition of Product, Grams | | | |
|---|---|---|---|---|---|---|---|---|---|---|---|
| | BZP | HNO$_3$ | H$_2$O | H$_2$SO$_4$ | SO$_3$ | | | DNBZP | H$_2$O | H$_2$SO$_4$ | SO$_3$ |
| I | 200 | 1080 | 120 | 0 | 0 | 1:0:0 | 100 | 299 | * | 0 | 0 |
| II | 110 | 75.6 | 35.9 | 1348 | 0 | 1:12.2:0 | 99 | 163.7 | * | * | 0 |
| III | 200 | 148.5 | 16.5 | 1965 | 570 | 1:9.8:2.9 | (a) 93 | 280** | 0 | 2563 | 321 |
| | | | | | | | (b) * | * | * | * | * |
| | | | | | | | (c) * | * | * | * | * |
| | | | | | | | (d) 84 | 252 | 0 | 2563 | 321 |
| IV | 200 | 148.5 | 16.5 | 890 | 55 | 1:4.5:0.3 | 100 | 229 | * | 957 | 0 |

TABLE I-continued

| Run No. | | | | | | | | | | |
|---|---|---|---|---|---|---|---|---|---|---|
| V | 200 | 148.5 | 16.5 | 1874 | 254 | 1:9.3:1.3 | 100 | 299 | 0 | 2090 | 77 |
| VI | 200 | 148.5 | 16.5 | 1934 | 316 | 1:9.7:1.6 | 96 | 287 | 0 | 2239 | 67 |
| VII | 200 | 148.5 | 16.5 | 2258 | 496 | 1:11.3:2.5 | 94 | 281 | 0 | 2563 | 180 |
| VIII | 200 | 148.5 | 16.5 | 1184 | 344 | 1:5.9:1.7 | 97 | 292 | 0 | 1489 | 95 |
| IX | 200 | 148.5 | 16.5 | 1035 | 509 | 1:5.2:2.5 | 74 | 220 | 0 | 1340 | 260 |
| X | 200 | 148.5 | 16.5 | 841 | 414 | 1:4.2:2.1 | 84 | 251 | 0 | 1146 | 165 |

| Run No. | Weight Ratio DNBZP:H₂SO₄:SO₃ | Weight Ratio of SO₃ In Product (Calculated) | DNBZP Isomer Distribution | | | | |
|---|---|---|---|---|---|---|---|
| | | | o,o' | o,m' | m,m' | m,p' | p,p' |
| I | 1:0:0 | 0 | 7.9 | 29.7 | 44.4 | 17.2 | 0.8 |
| II | * | 0 | 2.5 | 20.6 | 65.2 | 11.7 | <0.1 |
| III (a) | 1:8.1:1.1 | 11.1 | 0 | 12.1 | 82.2 | 5.7 | 0 |
| (b) | * | * | 0 | 11.1 | 82.9 | 6.0 | 0 |
| (c) | * | * | 0 | 5.0 | 89.1 | 5.9 | 0 |
| (d) | 1:8.1:1.1 | 11.1 | 0 | 0 | 93.7 | 6.3 | 0 |
| IV | 1:3.2:0 | 0 | 0.5 | 19.7 | 68.1 | 11.7 | <0.1 |
| V | 1:6.95:0.26 | 3.1 | 1.3 | 18.5 | 70.3 | 9.8 | 0.1 |
| VI | 1:7.8:0.23 | 2.6 | 1.5 | 17.0 | 71.5 | 10.0 | <0.1 |
| VII | 1:9.1:0.64 | 5.9 | 0 | 14.7 | 77.0 | 8.3 | 0 |
| VIII | 1:5.1:0.3 | 5.0 | 0 | 13.2 | 80.1 | 6.7 | 0 |
| IX | 1:6.1:1.2 | 14.3 | 0 | 0 | 93.5 | 6.5 | 0 |
| X | 1:4.6:0.7 | 10.5 | 0 | 1.5 | 90.4 | 8.1 | 0 |

BZP = Benzophenone
DNBZP = Dinitrobenzophenone
*Not taken
**Based on analysis of an aliquot portion The data in Table I shows the uniqueness of the process defined and claimed herein. In each of Examples I and II, wherein no sulfur trioxide was present, the amount of m,m'-dinitrobenzophenone was below the amount desired and the amount of dinitrobenzophenones containing an ortho nitro substituent was exceedingly high. Even though sulfur trioxide was present in the feed in each of Examples IV, V and VI, the weight ratio of benzophenone, sulfuric acid and sulfur trioxide in the feed was not in the critically-defined range, and therefore only relatively slight increases in the amount of m,m'-dinitrobenzophenone and only relatively slight decreases in o,m'-dinitrobenzophenone content was noted. In each of the remaining examples, however, which fall within the process defined herein, the amount of m,m'-dinitrobenzophenone in the dinitrobenzophenone product was greatly increased. In all cases no o,o'-dinitrobenzophenone was found and the amount of o,m'-dinitrobenzophenone was greatly decreased. In fact, in each of Examples III(d) and IX no dinitrobenzophenones containing an ortho nitro substituent were found.

In Example III it is shown that as the reaction progresses at the higher temperatures, the amount of o,m'-dinitrobenzophenone is greatly decreased, resulting in a final product wherein the percentage of m,m'-dinitrobenzophenone is greatly enhanced. That comparable results can be obtained by maintaining the reaction mixture at a lower temperature level but for extended periods of time is shown below in Example XI.

EXAMPLE XI

A total of 20 grams of benzophenone was dissolved, over a period of 0.5 hours, in 100 milliliters of oleum containing sulfuric acid and 22.5 weight percent sulfur trioxide. To this mixture there was added, over a period of 35 minutes, a mixture previously prepared by mixing 11 milliliters of 90 percent aqueous nitric acid and 30 milliliters of oleum containing sulfuric acid and 22.5 weight percent sulfur trioxide at a temperature of about 10° to about 20° C. The resulting mixture was stirred and allowed to react for 69 hours while maintaining the temperature of the reaction mixture at about 25° C. During the course of the reaction, the reaction mixture was monitored by HPLC. The data obtained are tabulated below in Table II.

TABLE II

| Reaction Time, Hours | Weight Percent Mononitro- benzophenones | Distribution of Dinitrobenzo- phenones, Weight Percent | | |
|---|---|---|---|---|
| | | o,m' | m,m' | m,p' |
| 0.5 | 11.9 | 12.5 | 81.5 | 6.0 |
| 4.0 | 4.7 | 11.2 | 82.9 | 5.9 |
| 69.0 | 2.2 | 7.3 | 87.0 | 5.7 |

Obviously, many modifications and variations of the invention, as hereinabove set forth, can be made without departing from the spirit and scope thereof and, therefore, only such limitations should be imposed as are indicated in the appended claims.

We claim:

1. A process for preparing m,m'-dinitrobenzophenone which comprises reacting benzophenone with nitric acid in oleum wherein the weight ratios of benzophenone, sulfuric acid and sulfur trioxide in the feed are in the range of about 1:2:2 to about 1:15:4.

2. The process of claim 1 wherein said oleum comprises a mixture of sulfuric acid and sulfur trioxide wherein the weight percent sulfur trioxide therein is in the range of about five to about 65 percent.

3. The process of claim 1 wherein said oleum comprises a mixture of sulfuric acid and sulfur trioxide wherein the weight percent sulfur trioxide therein is in the range of about 10 to about 35 percent.

4. The process of claim 1 wherein said process is carried out in a temperature range of about 5° to about 120° C. for about 10 minutes to about 120 hours, or even longer.

5. The process of claim 1 wherein said process is carried out in a temperature range of about 10° to about 90° C. for about one-half to about 24 hours.

6. The process of claim 1 wherein said process is carried out in at least two stages, in the first of which at a temperature of about 5° to about 50° C., for about 10 minutes to about 10 hours, and in a second stage at a temperature of about 20° to about 120° C. for about one-half to about five hours.

7. The process of claim 1 wherein said process is carried out in at least two stages, in the first of which at a temperature of about 10° to about 30° C. for about one-half to about eight hours, and in a second stage at a temperature of about 50° to about 90° C. for about one to about three hours.

8. The process of claim 1 wherein at the end of the reaction the reaction mixture contains in excess of about four weight percent sulfur trioxide.

9. The process of claim 1 wherein at the end of the reaction the reaction mixture contains about 10 to about 15 weight percent sulfur trioxide.

* * * * *